(12) United States Patent
Tkachuk

(10) Patent No.: US 8,742,370 B2
(45) Date of Patent: Jun. 3, 2014

(54) GAS SENSOR

(75) Inventor: Michael Tkachuk, Sayville, NY (US)

(73) Assignee: BAH Holdings LLC, Glen Cove, NY (US)

( * ) Notice: Subject to any disclaimer, the term of this patent is extended or adjusted under 35 U.S.C. 154(b) by 128 days.

(21) Appl. No.: 13/426,494

(22) Filed: Mar. 21, 2012

(65) Prior Publication Data

US 2013/0248736 A1 Sep. 26, 2013

(51) Int. Cl.
*F21V 9/16* (2006.01)
(52) U.S. Cl.
USPC ..................................... 250/458.1
(58) Field of Classification Search
USPC ..................................... 250/458.1
See application file for complete search history.

(56) References Cited

U.S. PATENT DOCUMENTS

| | | | |
|---|---|---|---|
| 4,632,807 A * | 12/1986 | Marsoner | 422/82.08 |
| 5,030,009 A * | 7/1991 | Ando et al. | 356/417 |
| 6,254,831 B1 * | 7/2001 | Barnard et al. | 422/82.08 |
| 6,330,464 B1 * | 12/2001 | Colvin et al. | 600/316 |
| 6,605,804 B1 * | 8/2003 | Muller-Fiedler et al. | 250/227.23 |
| 7,067,320 B2 * | 6/2006 | Klimant | 436/74 |
| 7,180,595 B2 * | 2/2007 | Willing et al. | 356/437 |
| 2002/0028518 A1 * | 3/2002 | Brinz et al. | 436/172 |
| 2004/0161853 A1 * | 8/2004 | Yang et al. | 436/164 |
| 2008/0161710 A1 * | 7/2008 | Gunneson et al. | 600/532 |
| 2008/0239322 A1 * | 10/2008 | Hodgkinson et al. | 356/437 |
| 2009/0206278 A1 * | 8/2009 | Hamner | 250/459.1 |
| 2010/0036272 A1 * | 2/2010 | Mace et al. | 600/531 |
| 2012/0057161 A1 * | 3/2012 | Tkachuk et al. | 356/437 |
| 2013/0023782 A1 * | 1/2013 | Karlsson | 600/532 |

* cited by examiner

*Primary Examiner* — David Porta
*Assistant Examiner* — Taeho Jo
(74) *Attorney, Agent, or Firm* — James P. Muraff; Neal, Gerber & Eisenberg LLP

(57) ABSTRACT

In one aspect of the disclosure, a gas sensor is provided, comprising: a chamber for containing a gas sample in use, and a radiation source adapted to emit radiation within a first waveband. A photoluminescent material, upon absorption of radiation of a first wavelength within the first waveband, emits radiation of a second wavelength, the photoluminescent material being responsive to the presence of a target gas species in the gas sample. The gas sensor further comprises a luminescence detector assembly. The luminescence detector assembly is adapted to detect radiation of the second wavelength and output a corresponding measurement signal related to the concentration of the target gas species. An optics assembly is adapted to receive radiation emitted by the radiation source and to converge the radiation towards a location at which the luminescence detector assembly cannot receive radiation.

44 Claims, 6 Drawing Sheets

GAS SENSOR

FIELD OF INVENTION

The present invention relates to optical gas sensors which utilise a gas-sensitive, photoluminescent material to determine the concentration of a gas of interest. Their operation is based on the fact that the intensity of the luminescence emitted by the photoluminescent material of the sensor depends on the concentration of the gas of interest. More particularly, the invention relates to improvement in design and performance of such sensors.

BACKGROUND

Luminescent (e.g. fluorescent) optical sensors are widely used in medicine, food processing and HVAC systems for determining the concentration of different gases such as oxygen, carbon dioxide and others. Examples of conventional fluorescent optical sensors are disclosed in U.S. Pat. No. 6,682,935 and U.S. Pat. No. 5,728,422.

FIG. 1 depicts a representative example of a conventional sensor. A radiation source 1 such as a light-emitting diode illuminates a gas-sensitive, photoluminescent layer 2, which here is supported on a backing film. In response to at least one wavelength emitted by the source 1, the layer 2 luminesces, emitting radiation at a different wavelength. The intensity of emitted luminescence depends not only on the intensity of incident radiation from the source 1 but also on the concentration of a target gas in the vicinity of the layer 2. A photo detector 3 receives luminescence emitted by layer 2 inside a spatial angle 4. The detector 3 is responsive to the emitted luminescence wavelength and outputs a measurement signal related to the detected intensity, and hence to the concentration of the target gas. Typically a focusing system 5 is provided to focus the radiation onto detector 3 via an optical filter 6.

The light-emitting diode (LED) or other radiation source 1 emits electromagnetic radiation across a waveband including specific wavelengths of which one or more will be absorbed by the gas sensitive layer 2 and give rise to photoluminescence. Typically the emitted luminescence will have a longer wavelength than those absorbed by the layer. However, the luminescent wavelength may be close to the waveband emitted by the LED or could even fall within the waveband, and as such the waveband to which the detector 3 is responsive will typically overlap that of the LED. As shown in FIG. 1, some of the radiation from the LED 1 passes though the sensitive layer 2 to the detector 3 and hence it is necessary to provide an optical filter 6 in order to suppress the high intensity LED emission and allow the luminescence to pass through, so as to distinguish the luminescence from the LED radiation. The degree of suppression achieved by the filter 6 must be high because generally the luminescence is relatively weak. In particular, in order to increase the efficiency of the sensor, the radiation source 1 often incorporates its own focusing system (not shown), which concentrates the LED radiation onto a spot on the sensitive layer 2, leading to a difference between the intensities of the LED radiation and the luminescence which could be more than four or five orders of magnitude. This means that the filter 6 must be a high quality optical filter, such as an interference filter for instance. Filters of this sort are complex to manufacture and expensive.

In some conventional sensors, the optical scheme is modified from the linear arrangement depicted in FIG. 1 to a more compact scheme in which both the radiation source 1 and detector 3 are placed on the same side of the gas sensitive layer 2. FIG. 2 shows an example, using like reference numerals for like components already described in relation to FIG. 1. In certain regards, a non-linear optical scheme such as this has better protection from direct LED radiation exposure, because at least no straight-forward light from the LED is received at detector 3. However, the required degree of LED radiation suppression is still high since there is a lot of scattered light and hence it is still necessary to provide a high quality optical filter 6.

SUMMARY OF INVENTION

In accordance with a first aspect of the present invention, a gas sensor comprises:

a chamber for containing a gas sample in use;

a radiation source adapted to emit radiation within a first waveband;

within the chamber and positioned to receive radiation from the radiation source, a photoluminescent material which, upon absorption of radiation of a first wavelength within the first waveband, emits radiation of a second wavelength, the photoluminescent material being responsive to the presence of a target gas species in the gas sample such that the intensity of the emitted radiation varies according to the concentration of the target gas species in the gas sample;

a luminescence detector assembly positioned at a first location at which radiation emitted by the photoluminescent material can be received, the luminescence detector assembly being adapted to detect radiation of the second wavelength and output a corresponding measurement signal related to the concentration of the target gas species in the gas sample; and an optics assembly adapted to receive radiation emitted by the radiation source and to converge the radiation towards a second location at which the luminescence detector assembly cannot receive radiation.

By using an optics assembly to converge (e.g. focus) the radiation emitted by the radiation source away from the luminescence detector assembly in this way, the intensity of such "source" radiation arriving at the detector is significantly reduced. As such, the need for high suppression of the source radiation is correspondingly reduced, and sufficient optical filtering can be achieved by a simple and inexpensive filter such as a semi-transparent film of appropriate colour. In some cases, the need for a filter may be avoided altogether.

The photoluminescent material will emit radiation in all directions upon illumination and hence the detector can be positioned to receive the luminescence at any location different from that towards which the source radiation is converged. In some cases the luminescence could also undergo a degree of convergence by the optics assembly prior to detection, e.g. being focussed towards a different position from that of the source radiation, but in preferred embodiments, the photoluminescent material, the optics assembly and the luminescence detector assembly are positioned relative to one another such that the luminescence detector assembly receives radiation emitted by the photoluminescent material which has not undergone convergence by the optics assembly. For example, the photoluminescent material may be on the same side of the optics assembly as the detector, or could be applied to a surface of the optics assembly such that emitted radiation will not be converged significantly. In most preferred embodiments, the photoluminescent material, the optics assembly and the luminescence detector assembly are positioned relative to one another such that the luminescence detector assembly receives radiation directly from the photoluminescent material which has not been passed via the optics assembly.

The stronger the convergence achieved by the optics assembly, the less source radiation will be incident on the luminescence detector assembly. In particularly preferred embodiments, therefore, the optics assembly is a focussing optics assembly adapted to focus radiation received from the radiation source on to the second location. That is, the focussing optics assembly forms an image of the radiation source at the second location. This constitutes a very high degree of convergence with little or no source radiation arriving elsewhere. However, optics assemblies which do not fully focus the radiation can still be used to achieve reasonable convergence and hence benefits as described above.

Any type of optics assembly capable of converging the source radiation in the manner described could be utilised. For instance, a lens assembly of the sort depicted in FIGS. 1 and 2 could be used with the detector offset from the focal position shown. However, in preferred embodiments, the optics assembly is a reflective optics assembly adapted to reflect radiation received from the radiation source such that the second location towards which the radiation is converged is on the same side of the optics assembly as the radiation source. Most preferably, the luminescence detector assembly is positioned on the same side of the optics assembly as the radiation source and the second location, the first location at which radiation emitted by the photoluminescent material can be received by the luminescence detector assembly being laterally offset from the second location in a direction perpendicular to the optic axis of the optics assembly. This results in a particularly compact arrangement, with both electronic components on the same side of the sensor which assists in the manufacturing process.

Advantageously, in a lateral plane perpendicular to the optic axis of the optics assembly, the first location at which luminescence can be received by the luminescence detector assembly substantially surrounds the second location. Thus, the source radiation is substantially localised onto the second location whilst luminescence emitted by the gas-sensitive, photoluminescent material can be received and detected across the majority of the surrounding area. A large surface area of the detector assembly allows for detection of a large proportion of the emitted luminescence and hence enhances the sensitivity of the sensor.

In particularly preferred embodiments, the photoluminescent material is disposed between the radiation source and the reflective optics assembly such that radiation passes through the material at least twice from the radiation source to the second location. Source radiation can be absorbed by the material on each pass, leading to a corresponding increase in the intensity of emitted luminescence. For instance, the efficiency of converting source radiation into luminescence will be at least doubled relative to conventional optical schemes. This further improves the sensitivity of the device. The photoluminescent material may be disposed on a surface of the optics assembly, for example.

A number of different measures may be taken to prevent radiation arriving at the second location from being incident on the luminescence detector assembly. In some preferred embodiments, the luminescence detector assembly is absent at the second location. In other words, the optical path followed by the converging source radiation is simply not coincident with the luminescence detector assembly.

In a particularly preferred implementation making use of a reflective optics assembly, the second location is coincident with the radiation source, such that the optics assembly converges the reflected radiation towards the radiation source. Thus, the source radiation is effectively trapped between the LED or other radiation source and the optics assembly. Luminescence emitted by the gas-sensitive material, on the other hand, will travel in all directions and can therefore be detected by the detector assembly.

As noted above, the luminescence detector assembly could simply be absent in the vicinity of the radiation source, e.g. arranged to surround it in the same plane. However, in other embodiments, the radiation source is positioned between the luminescence detector assembly and the optics assembly, the radiation source obstructing the converged radiation from reaching the luminescence detector assembly. Thus, the detector assembly may extend under the radiation source which effectively shields it from the source radiation. This enables the use of a conventional, large surface area detector assembly without any need for modification.

In further preferred embodiments, a additional component may be provided to receive the converged source radiation instead of the radiation source. Preferably, a radiation mask is positioned at the second location, such that the optics assembly converges the radiation towards the radiation mask. The radiation mask could comprise, for example, a plate or layer of substantially opaque material such as metal or plastic, which may absorb or reflect the source radiation. Preferably the mask comprises a radiation absorber in order to minimise any stray reflections. The mask could comprise a cavity, blackbody or any radiation-absorbing layer. In yet further embodiments, discussed below, the mask could have additional functionality. More than one mask could be provided, e.g. if there is more than one second location towards which the optics assembly converges the source radiation (e.g. an elliptical mirror with two foci).

In particularly preferred embodiments, the radiation mask is adapted to absorb radiation of at least the first wavelength, preferably radiation across the waveband emitted by the radiation source. This prevents further reflections of the source radiation, which may be undesirable.

As in the case where the source radiation is collated onto the radiation source, the mask can be laterally offset from the luminescence detector assembly (e.g. in the same plane), or can be used to shield the detector whereby the radiation mask is positioned between the luminescence detector assembly and the optics assembly, the radiation mask obstructing the converged radiation from reaching the luminescence detector assembly.

Radiation masks of this sort can be utilised in transmissive implementations (e.g. where the optics assembly is lens-based) but preferably the optics assembly is a reflective optics assembly adapted to reflect radiation received from the radiation source such that the second location towards at which the radiation mask is positioned is on the same side of the optics assembly as the radiation source. In particularly preferred cases, the radiation source and radiation mask are located in substantially the same lateral plane perpendicular to the optics assembly. For optimum performance, the optics assembly is preferably a focussing optics assembly and the lateral plane in which the radiation source and radiation mask are positioned is a focal plane of the optics assembly.

In particularly advantageous embodiments, the radiation mask comprises a source radiation detector adapted to detect radiation within the first waveband and to output a corresponding signal representing a reference signal. Thus, the source radiation is converged or focussed onto a second detector which both acts to absorb the source radiation in the manner already described and outputs a signal representative of the performance of the LED or other radiation source. This provides a reference channel against which the measurement signal from the luminescence detector assembly can be compared to remove distortions caused by changes in the intensity of the source radiation, which is a major cause of signal drift. This substantially improves the accuracy and stability of the sensor.

The reference channel can alternatively be enabled by providing a source radiation detector positioned at a third location at which radiation emitted by the radiation source can be received, the source radiation detector being adapted to detect radiation within the first waveband and to output a corresponding signal representing a reference signal. For instance, the source radiation detector could be positioned to intercept a portion of the radiation emitted by the LED or other source before it reaches the optics assembly. The source radiation detector is preferably positioned such that luminescence from the photoluminescent material is not significantly received and a shield and/or filter may be provided for this purpose. However, since the source radiation is typically of a much greater intensity than the luminescence, this is not essential.

Where the sensor further comprises a source radiation detector positioned at the second location or a third location at which radiation emitted by the radiation source can be received, the source radiation detector being adapted to detect radiation within the first waveband and to output a corresponding signal representing a reference signal, a processor is preferably provided which is adapted to compute the ratio between the measurement signal and the reference signal and to output a normalised measurement signal based on the ratio.

In one example, where the optics assembly is a reflective optics assembly adapted to reflect radiation received from the radiation source such that the second location towards at which the radiation mask is positioned is on the same side of the optics assembly as the radiation source, the reflective optics assembly has a non-reflective window through which a portion of the radiation emitted from the radiation source may be transmitted to the third location. Alternatively the source radiation detector could be disposed on the surface of the optics assembly.

The optics assembly could be constructed in various different ways. In reflective implementations, the assembly preferably comprises a concave mirror or a converging lens system and mirror in combination. Preferably, to enhance convergence of the source radiation, the concave mirror comprises a dome-shaped mirror, at least a section of a spherical mirror, a hemispherical mirror, an elliptical mirror or a parabolic mirror. Mirrors shaped so as to provide one or more geometrical focus positions are preferred for the reasons discussed above.

In particularly preferred examples, the optics assembly comprises a concave mirror which subtends a solid angle at the radiation source greater than or equal to the angular spread of the radiation emitted from the source. In this way, substantially all of the radiation emitted by the source is collected by the optics assembly thereby minimising the amount of radiation lost from the sensor and enabling the photoluminescent material to receive a greater proportion of the source radiation. As a result, the material is able to emit a higher intensity of luminescent, enabling the sensor to respond correctly across a greater range of gas concentrations since there is no saturation or quenching imposed by the source radiation levels. For example, the radiation source may be positioned inside the concave mirror.

The photoluminescent material could be located anywhere at which source radiation will be incident upon it (whether or not the source radiation has yet reached the optics assembly) and which is visible to the luminescence detector assembly. For example, the material could be provided on a support layer between the radiation source and a reflective optics assembly. However in preferred embodiments, the material is disposed on a surface of the optics assembly, e.g. as a thin layer. In this way, the part count is reduced and also the number of surfaces through which the radiation travels is minimised, which could otherwise lead to undesirable scattering.

In particularly preferred embodiments, the optics assembly is a reflective optics assembly having an axis of rotational symmetry, the radiation source and second location being disposed on the axis of rotational symmetry. For instance, in the case of a spherical mirror this arrangement will lead to the source radiation being collected onto the radiation source as mentioned above. Alternatively, the radiation source and second location may be laterally offset from the axis of rotational symmetry by equal and opposite amounts. This is particularly preferable where a source radiation detector is provided at the second location.

A single luminescence detector could be provided, but preferably the luminescence detector assembly comprises a plurality of detectors, e.g. arranged in a matrix. The detectors could be connected in series or in parallel. The use of multiple detectors makes it possible to extend the assembly over a large surface area without the need for bespoke components.

In particularly preferred embodiments, the luminescence detector assembly, radiation source and radiation mask if provided form an array in substantially the same plane. For example, a grid of components could be formed with the luminescence detectors replaced where necessary by an LED or other radiation source and mask unit or source radiation detector as desired. In this way, all of the electric components can be formed together as a single unit thereby enabling fast throughput manufacture.

As already mentioned, by converging the source radiation in the manner described it may be possible to omit optical filters from the design entirely. However, in many cases the convergence or focusing will not prevent 100% of the source radiation from reaching the luminescence detector and hence filters may still be included. Nonetheless, the requirements placed on the filters are greatly reduced as compared with conventional sensors: for instance, semi-transparent plastic films of appropriate colours may be sufficient. Where the components are formed into an array, a housing for holding the components in position may be formed of suitably coloured plastic to provide the desired filtering effects. Thus in certain embodiments the sensor further comprises a filter positioned to filter radiation arriving at the luminescence detector assembly and adapted to obstruct the passage of radiation in the first waveband. Likewise, a filter may be positioned to filter radiation emitted by the radiation source to obstruct the passage of radiation of the second wavelength.

Preferably, the radiation source comprises a LED, laser diode, defocused laser diode or incandescent bulb.

In accordance with a second aspect of the invention, a gas sensor is provided comprising:

a chamber for containing a gas sample in use;

a radiation source adapted to emit radiation within a first waveband, the radiation being emitted across a first solid angle;

within the chamber and positioned to, receive radiation from the radiation source, a photoluminescent material which, upon absorption of radiation of a first wavelength within the first waveband, emits radiation of a second wavelength, the photoluminescent material being responsive to the presence of a target gas species in the gas sample such that the intensity of the emitted radiation varies according to the concentration of the target gas species in the gas sample;

a luminescence detector assembly positioned at a first location at which radiation emitted by the photoluminescent material can be received, the luminescence detector assembly being adapted to detect radiation of the second wavelength and output a corresponding measurement signal related to the concentration of the target gas species in the gas sample; and a concave mirror assembly adapted to direct radiation from the radiation source towards the photoluminescent material, wherein the concave mirror assembly subtends a solid angle at the radiation source substantially equal to or greater than the first solid angle such that substantially all of the radiation emitted by the source is directed towards the photoluminescent material.

By utilising a concave mirror assembly of this sort, substantially all of the radiation emitted by the source is received by the photoluminescent material. As described above, this increases the sensitivity and range of the sensor since the amount of emitted luminescence will not be curbed as a result of the source.

Preferably, the photoluminescent material is disposed between the radiation source and the reflective optics assembly such that radiation from the source passes through the material at least twice. This further enhances the efficiency of conversion of source radiation into luminescence and increases the sensor sensitivity as described above.

In particularly preferred embodiments, the concave mirror assembly subtends a solid angle at the radiation source of at least $\pi/2$, preferably at least $\pi$, still preferably at least $2\pi$. For example, the radiation source may be located inside the concave mirror. Advantageously, the concave mirror assembly comprises a dome-shaped mirror, at least a section of a spherical mirror, a hemispherical mirror, an elliptical mirror, a parabolic mirror, or a prismatic mirror.

This arrangement can be implemented without an optics assembly which converges the source radiation if desired. If so, high quality filters will be required and the sensor preferably further comprises a filter positioned to filter radiation arriving at the luminescence detector assembly and adapted to obstruct the passage of radiation in the first waveband. Likewise a filter may be positioned to filter radiation emitted by the radiation source to obstruct the passage of radiation of the second wavelength.

In accordance with a third aspect of the invention, a gas sensor is provided comprising:

a chamber for containing a gas sample in use;

a radiation source adapted to emit radiation within a first waveband;

within the chamber and positioned to receive radiation from the radiation source, a photoluminescent material which, upon absorption of radiation of a first wavelength within the first waveband, emits radiation of a second wavelength, the photoluminescent material being responsive to the presence of a target gas species in the gas sample such that the intensity of the emitted radiation varies according to the concentration of the target gas species in the gas sample;

a luminescence detector assembly positioned to receive radiation emitted by the photoluminescent material, the luminescence detector assembly being adapted to detect radiation of the second wavelength and output a corresponding measurement signal related to the concentration of the target gas species in the gas sample;

a source radiation detector assembly positioned to receive radiation emitted by the radiation source and adapted to detect radiation of the first waveband and output a corresponding reference signal; and a processor adapted to compute the ratio between the measurement signal and the reference signal and to output a normalised measurement signal based on the ratio.

As described above, by providing a reference channel in this way, variations in the radiation output by the LED or other source can be compensated for. This significantly improves the accuracy and stability of the sensor.

This arrangement can be implemented without an optics assembly which converges the source radiation if desired. If so, high quality filters will be required and the sensor preferably further comprises a filter positioned to filter radiation arriving at the luminescence detector assembly and adapted to obstruct the passage of radiation in the first waveband. Likewise a filter may be positioned to filter radiation emitted by the radiation source to obstruct the passage of radiation of the second wavelength. Another filter may also be positioned to filter radiation arriving at the source radiation detector assembly to obstruct the passage of radiation of the second wavelength.

BRIEF DESCRIPTION OF THE DRAWINGS

Examples of gas sensors in accordance with the presently disclosed principles will now be described and contrasted with conventional sensors with reference to the accompanying drawings, in which.

DETAILED DESCRIPTION OF PREFERRED EMBODIMENTS

As described above, luminescent optical gas sensors can be used to measure the concentration of various target gases, including oxygen and carbon dioxide, through the use of a photoluminescent material which is sensitive to the target gas in question. Suitable photoluminescent materials are known for example from U.S. Pat. No. 6,682,935 and U.S. Pat. No. 5,728,422, both of which documents are incorporated herein by reference. Any of the gas-sensitive materials disclosed in either document could be used as the photoluminescent material referred to in the description below. The photoluminescent material could be fluorescent and hence the terms "luminescence" and "fluorescence" may be used interchangeably below. Preferably, the material emits the luminescence substantially instantaneously upon source radiation striking the material.

Figure 1:
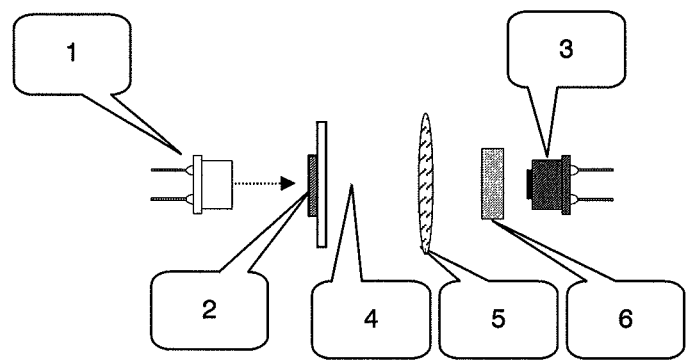
FIGS. 1 and 2 schematically depict examples of conventional gas sensors.
Figure 2:
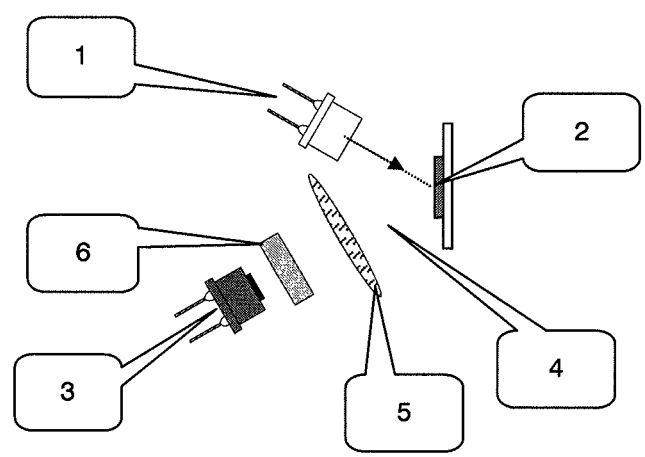
Figure 3:
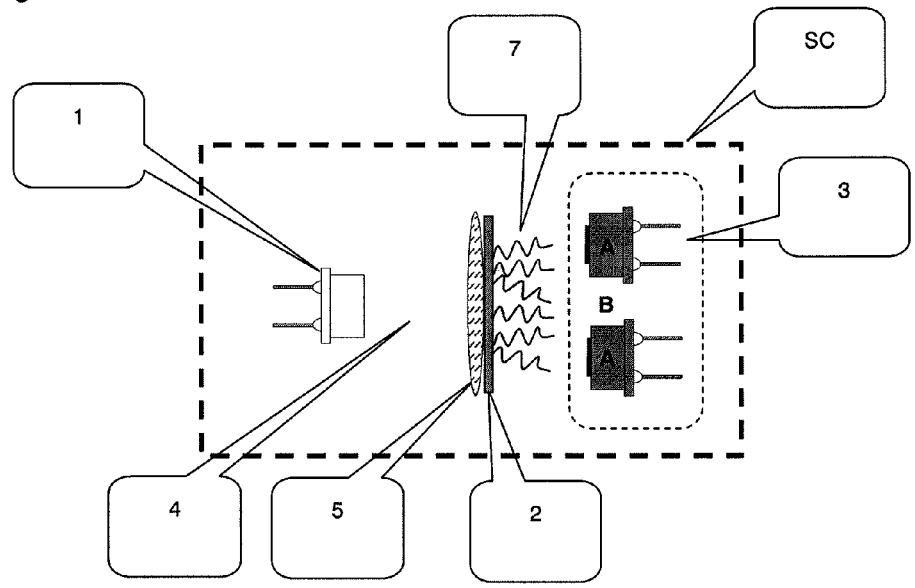
FIG. 3 illustrates a first embodiment of a gas sensor.

FIG. 3 shows a first embodiment of a gas sensor utilising the presently disclosed techniques. Like reference numerals are used for components already described above with reference to FIGS. 1 and 2. Here, the radiation source 1 is a LED although other sources such as a laser, defocused laser or incandescent bulb could be used instead. The source could emit monochromatic radiation but more typically will emit a range of wavelengths across a waveband $\Delta\lambda_1$. For example, a blue LED with an emission waveband from 440 nm to 550 nm may be used in an implementation of the sensor configured for the detection of oxygen. An optics assembly 5, here a lens system, converges the source radiation 4 by focusing it onto a location "B" at which an image of the LED 1 will be formed. A photoluminescence detector assembly 3 is provided, which here comprises two detectors at locations "A". The focussed source radiation 4 arriving at location B is not incident on either detector and hence does not contribute to the measurement signal output by the detector assembly 3. In contrast, luminescence 7 emitted by a layer of photoluminescent material 2 inserted into the optical path travels in all directions and is received by the detector assembly 3 giving rise to the measurement signal. In this example, the photoluminescent material is disposed between the optics assembly 5 and the detector assembly 3, within a chamber for containing a sample of gas in use (not shown), such that the emitted luminescence does not pass via the optics assembly 5 before striking the detector assembly 3. This is not essential but it is preferable that the emitted luminescence is not significantly converged by the optics assembly 5 before arriving at the detector assembly in order to preserve an offset between the first location A at which the luminescence is detected and the second location B towards which the source radiation 4 is converged. Conveniently, the photoluminescent material 2 is provided in the form of a layer disposed on one or both sides of the lens 5. This reduces the part count and also the number of surfaces present, which could other lead to increased scattering of the source radiation 4.

Figure 11:
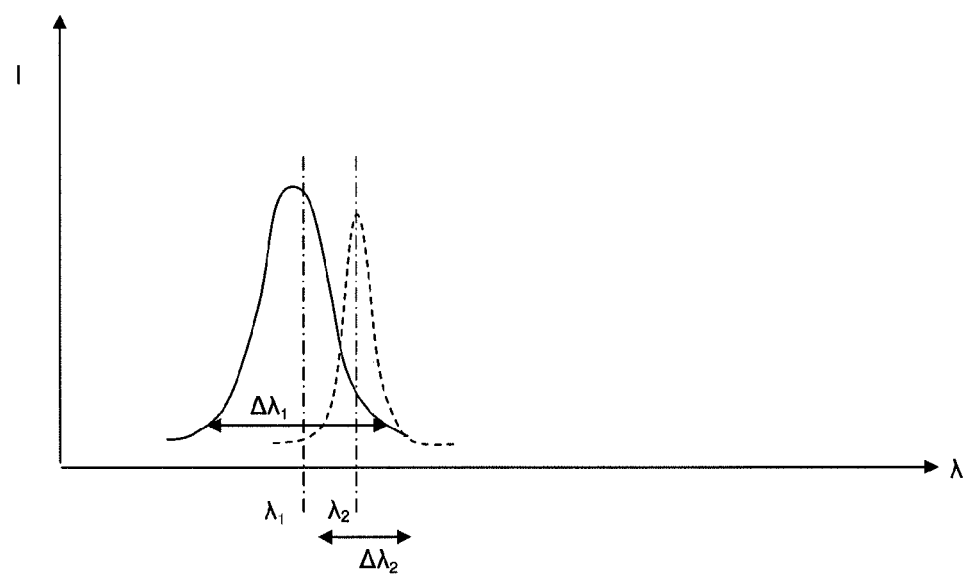
FIG. 11 is a plot illustrating an exemplary emission spectrum of a radiation source (solid line) and exemplary luminescence spectra of a gas-sensitive material (dashed lines).

With reference to FIG. 11, which provides illustrative wavelength spectra of the source radiation (solid line) and two alternative photoluminescent materials (dashed lines), the photoluminescent material 2 will respond to absorption of at least a first wavelength $\lambda_1$ emitted by the source 1 by emitting luminescence at a second different wavelength $\lambda_2$, typically longer than the first. The luminescence detector assembly 3 is thus configured to operate across a waveband $\Delta\lambda_2$ which includes the luminescence wavelength. $\lambda_2$. However, typically the detector waveband will overlap that emitted by the source 1, at least partially, meaning that any source radiation arriving at the detector assembly could distort the output signal, hence the requirement for a high quality optical filter in conventional devices. In the embodiment, by using an optics assembly to converge the source radiation 4 towards a position B at which the luminescence detector assembly 3 will not receive it, the need for any optical filtering of radiation arriving at the detector assembly 3 is greatly reduced or indeed eliminated.

In the first embodiment, the optics assembly achieves a very high degree of source radiation convergence due to the use of a focusing lens. Focussing optics assemblies such as these form an image of the radiation source 1 at a defined location which confines the large majority of the source radiation to that location. As such very little source radiation, if any, will be incident elsewhere, including on the detector assembly 3. However, whilst preferred, the use of a focussing optics assembly is not essential since other configurations in which the radiation is converged towards one or more defined locations will also achieve the desired benefits albeit to a lesser degree since whilst the proportion of source radiation falling on the detector assembly will be reduced, it may not be eliminated entirely. For example, whilst the intensity of the source radiation 4 should be highest at the one or more defined locations, it may not immediately drop to zero outside of those locations but rather there may be a gradual decrease.

Figure 4:
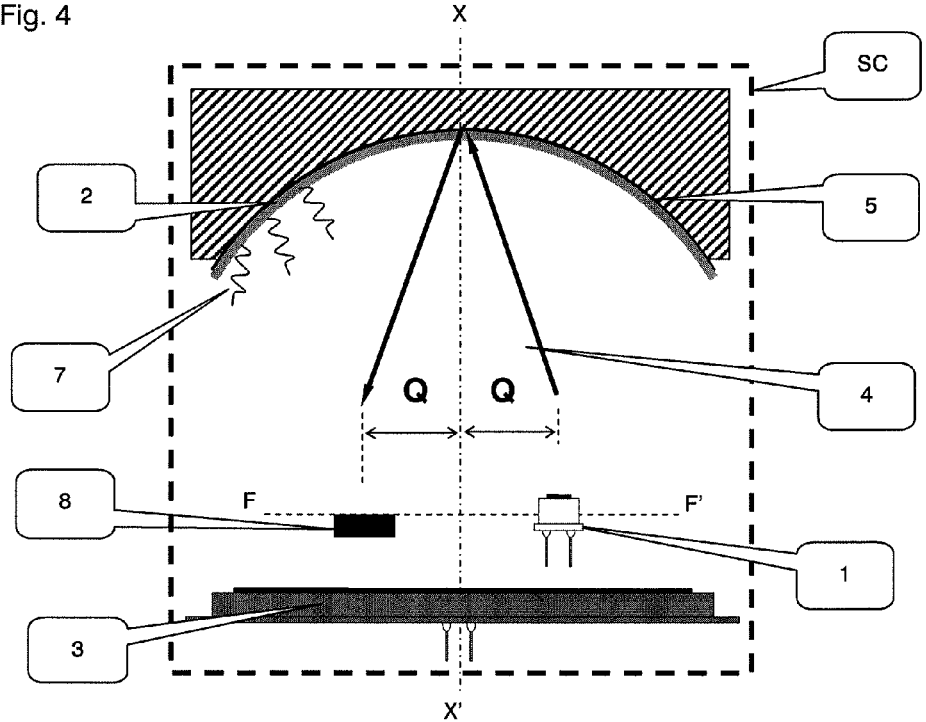
FIG. 4 illustrates a second embodiment of a gas sensor.

A second embodiment is depicted in FIG. 4, where rectangle SC represents a chamber for containing a gas sample in use. Here, the lens used in the first embodiment is replaced by a reflective optics assembly 5, comprising in this example a section of a spherical mirror. The use of a reflective optics assembly has a number of particular advantages. Firstly, all of the electronic components of the sensor can be located on the same side of the optics assembly allowing for a more compact design and also significantly simplifying the manufacturing process since the components can, if desired, be produced in the form of a single unit. Secondly, if the photoluminescent material 2 is disposed between the radiation source 1 and the mirror 5, the source radiation 4 will be passed at least twice through the material 2, which increases the efficiency of the sensor by at least a factor of 2. This is because the material is effectively exposed to at least twice the dosage of source radiation as compared with single-pass designs.

Further, the use of a concave mirror such as the spherical mirror shown is particularly beneficial since, as compared with flat mirrors or lenses, a greater proportion of the radiation emitted from source 1 will be captured. In practice, whilst the radiation source will produce a central high intensity, narrow beam, less intense radiation will still be emitted over a wide range of angles. The concave nature of the mirror collects more of this peripheral radiation for exposure of the photoluminescent material 2, which further increases the efficiency of the sensor.

Improving the sensor efficiency also extends the range of target gas concentrations over which the sensor can operate since the possibility of saturation or quenching of the sensor is reduced. This is because the amount of source radiation available will inherently limit the intensity of luminescence that can be produced: as the target gas concentration changes in such a way that the luminescent response of the material is increased, there will come a threshold at which this will not be reflected in the luminescent output of the material, because insufficient source radiation is available. Conversely, the lower the intensity of the source radiation, the earlier the material will cease emitting a detectable amount of luminescence as the target gas concentration changes to decrease the luminescent response of the sensor. Hence, the more efficiently the sensor transmits radiation from the source to the gas-sensitive material, the greater the operating range of the sensor.

A concave, reflective optics assembly such as mirror 5 can be utilised in otherwise conventional sensors if desired in order to attain these benefits in terms of improved efficiency independently of the other improvements discussed above.

Returning to FIG. 4, as in the first embodiment, here the optics assembly will focus the source radiation due to its spherical curvature. However, any other concave or dome-shaped mirror which collects the source radiation towards a defined position could be used instead. Elliptical or parabolic mirrors could alternatively be used (in the case of a parabolic mirror, the surface has just one focus point, so it cannot focus a divergent beam from a radiation source to any other point—however, a parabolic mirror will focus a parallel radiation beam, as will be emitted by a laser for example).

Photoluminescent material 2 is applied to the interior surface of the mirror 5. Radiation from a radiation source 1 passes through the photoluminescent material 2 and is converged by the mirror 5 towards a position at which an image of the source 1 will be formed. A radiation mask 8 is located at the image position which in the case of a spherical mirror will be in the same plane F-F' as that in which the source 1 is located (referred to hereinafter as the focal plane). Underlying the radiation source 1 and mask 8 is a luminescence detector assembly 3, which in this example comprises a single, large area detector.

Upon illumination by the source radiation 4, the photoluminescent material 2 emits radiation 7 in all directions which is not converged or focussed by the mirror 5. The luminescence 7 is incident on the detector assembly 3 across a large proportion of its surface area. The majority of the source radiation 4, however, is collected onto mask 8 which substantially blocks further passage of the radiation thereby preventing its receipt at the detector assembly 3. The radiation mask 8 can take any form which will obstruct the passage of radiation in the source waveband $\Delta\lambda_1$, such as an opaque plate of metal or plastic, or a similar layer applied to the surface of the detector assembly 3. Alternatively, the mask 8 could be specifically designed to absorb radiation of the appropriate wavelengths. For example, the mask could comprise a cavity or a blackbody. This could be implemented for instance by configuring the mask to define a hole or recess with its interior walls formed of or covered by a radiation-absorbing (typically black) material such as amorphous carbon, fabric or black paint. Alternatively, a plate of or covered by the same radiation-absorbing material would provide a similar result.

Where a spherical mirror is employed, in order to image the source 1 onto mask 8, the two components are preferably located in the same plane F-F' as one another, at equal and opposite positions from the symmetry axis X-X'. In this case, the two components are aligned on a diameter of the sensor, each spaced from the centre axis by a distance Q. Other geometries may be adopted depending on the optics assembly in use. For instance, an elliptical mirror will generate two focus positions and hence two radiation masks 8 may be provided, once to block the image formed at each of the positions.

Figure 5:
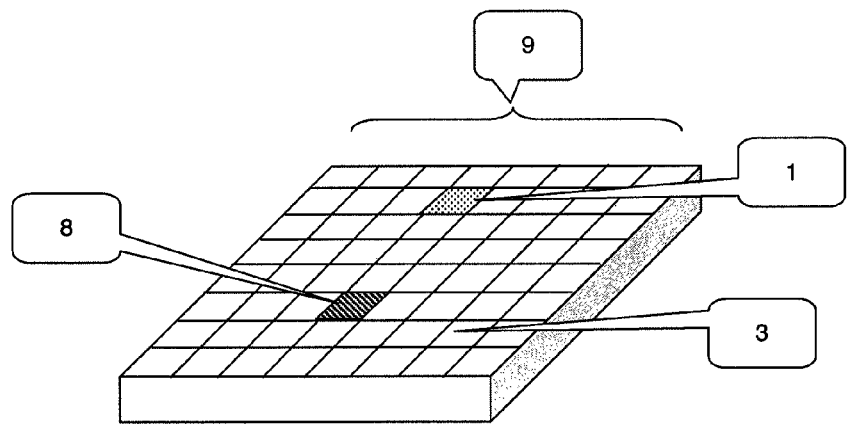
FIG. 5 shows an exemplary component array for use in the second embodiment.

In the example shown, the source 1 and mask 8 lie in one plane whilst the detector assembly 3 is arranged underneath. However, the detector assembly 3 could lie in any plane since the luminescence it receives is preferably unfocussed. In a particularly preferred variant, the detector assembly 3 lies in the same plane F-F' as the source 1 and mask 8, and the detector assembly is simply absent at each of those specific locations. FIG. 5 depicts a component array 9 suitable for this implementation. The array 9 comprises a grid of components which may be mounted for instance on a PCB or in a suitable housing. The unshaded components, of which one is labelled 3, are detectors which together make up the luminescence detector assembly, connected in series or in parallel. One space on the array is reserved for radiation source 1, and another at the appropriate, opposite position, carries mask 8 (which may overlie or replace entirely a detector). In this way, all of the electrical components of the sensor can be formed as an integral unit which greatly streamlines the manufacturing process and makes the design particularly well adapted for mass production.

Figure 6:
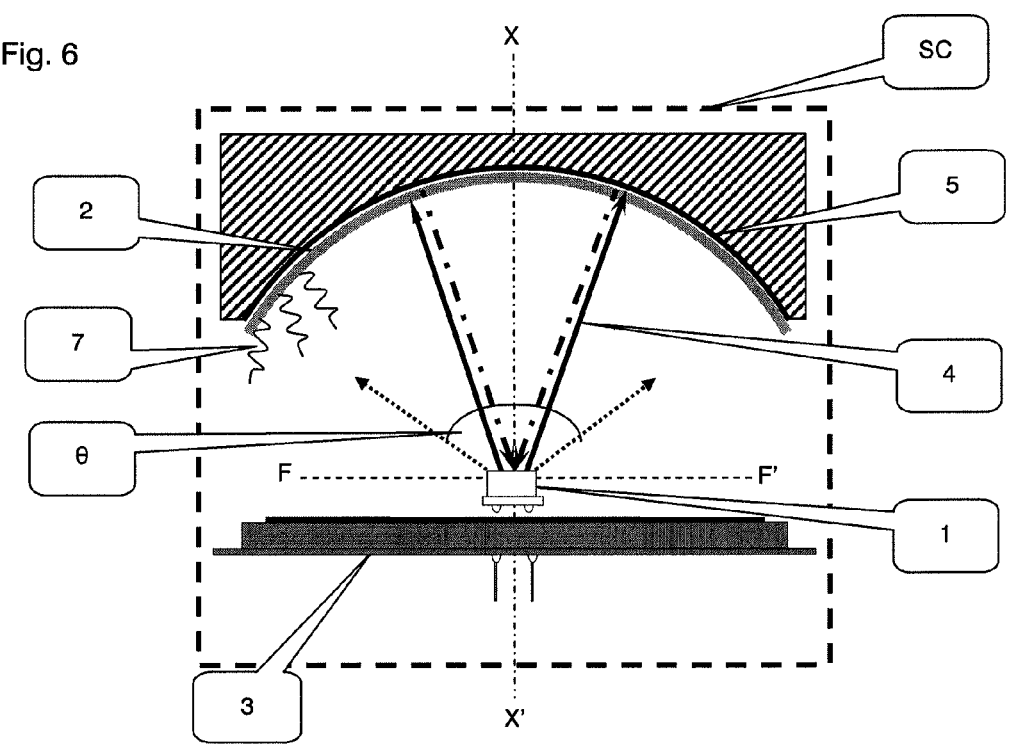
FIG. 6 illustrates a third embodiment of a gas sensor.

A third embodiment of a gas sensor is depicted in FIG. 6. As in the second embodiment, the optics assembly 5 comprises a section of a spherical mirror and the photoluminescent material 2 is disposed as a layer on its surface. The radiation source is positioned between the luminescence detector assembly 3 and the optics assembly. However, in this example, the source 1 is positioned such that it is co-incident with the image formed of the source by the mirror 5, i.e. on the symmetry axis X-X' (in the case of a spherical mirror). Thus the source radiation 4 is reflected by the mirror 5 directly back to the source 1, "locking" the source radiation 4 between the two components. The source 1 effectively acts as a radiation mask itself, obstructing passage of the reflected source radiation 4 to the detector 3, such that no additional mask component is required. The luminescence emitted by material 2, on the other hand, travels in all directions and thus is incident on the detector assembly at positions surrounding the radiation source 1.

As previously described, the use of a focussing optics assembly is preferred in this embodiment also in order that the large majority of the reflected source radiation is incident on the source 1 and ideally no source radiation reaches the detector assembly 3. However, optics assemblies which achieve a lesser degree of convergence could alternatively be used. Similarly, whilst in the example shown, the detector assembly 3 extends underneath the LED 1, in practice the detector assembly could be absent in the region of LED 1 and the two components could be disposed in the same plane as one another, optionally in the form of a component array similar to that shown in FIG. 5.

FIG. 6 also illustrates the increased collection efficiency of a concave mirror 5 as the optics assembly, mentioned above. The radiation source emits radiation over a solid angle θ and, in the most preferred embodiments, the solid angle subtended by the mirror 5 at the radiation source 1 will be substantially equal to, or greater than θ. In this way substantially all of the radiation emitted by source 1 will be collected for use in the sensor. For instance, in preferred cases, the subtended angle is at least $\pi/2$, preferably at least $\pi$, still preferably at least $2\pi$ (i.e. a hemisphere). Most preferably, the source 1 is located inside the concave cavity formed by the mirror 5, such that the mirror entirely covers and surrounds the source. These considerations are applicable whether or not the source 1 is located on the symmetry axis X-X'.

Figure 7:
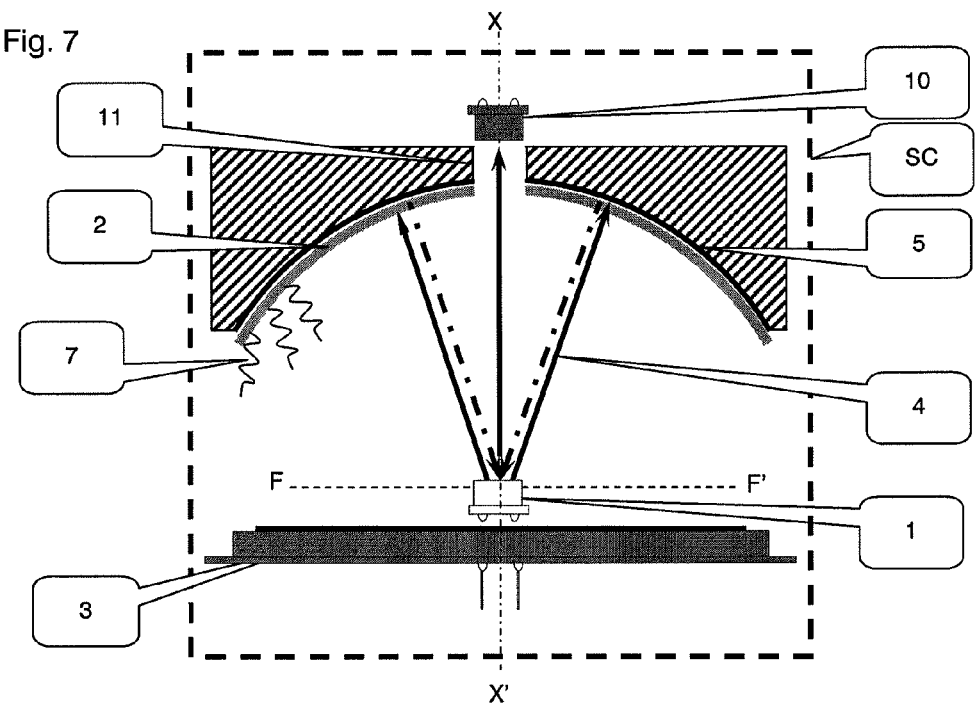
FIG. 7 illustrates a fourth embodiment of a gas sensor.

FIG. 7 depicts a fourth embodiment in which the optical geometry is identical to that of the third embodiment. The source 1, spherical mirror 5 and luminescence detector assembly 3 are each arranged in the manner already described with reference to FIG. 6, and the operation is the same. However, the fourth embodiment incorporates an additional detector 10 configured and positioned to detect the source radiation 4. Specifically, a window 11 is provided in mirror 5 through which radiation emitted by source 1 will be transmitted to the source radiation detector 10. The source radiation detector 10 is responsive to radiation within at least a part of the source waveband $\Delta\lambda_1$, preferably including at least the first wavelength $\lambda_1$.

Figure 9:
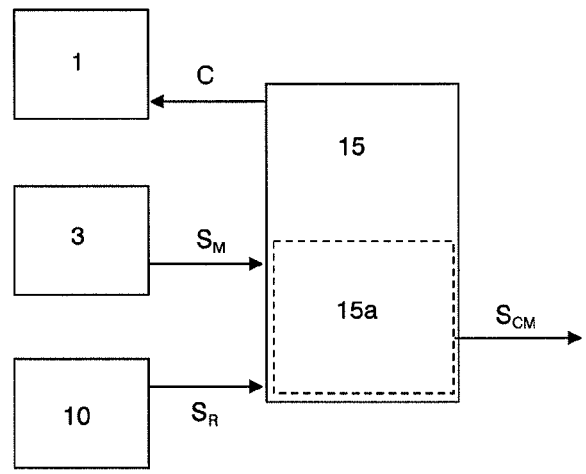
FIG. 9 is a block diagram depicting selected functional components of the fourth or fifth embodiments.

The source radiation detector 10 outputs a signal corresponding to the intensity of the radiation emitted from source 1, which can be used as a reference channel. The intensity of the emitted source radiation 4 tends to vary due to a number of factors including the working temperature and also the age of the LED or other source 1. Since the source radiation intensity has a direct impact on the amount of luminescence emitted by the gas-sensitive material 2, such variations will lead to distortions or drift in the measurement signal output by the luminescence detector assembly 3. By comparing the measurement signal against the reference signal from the source radiation detector 10, such variations can be identified and compensated for. With reference to FIG. 9, which is a block diagram showing selected functional components of the sensor, a processor 15 (internal or external to the sensor) may be provided including a portion 15a for calculating the ratio between the measurement signal $S_M$ and the reference signal $S_R$ to produce a normalised measurement signal $S_{CM}$ based on the ratio, i.e. $S_{CM}$ is proportional to $(S_M/S_R)$. This greatly improves the accuracy and stability of the measurements made using the sensor, since the ratio is independent of changes in the radiation source intensity, e.g. due to drift or aging, which may otherwise distort the output. The processor could take the form or hardware or software, e.g. a microprocessor, and may include other functions such as the control of radiation source 1 (control signal C).

Figure 8:
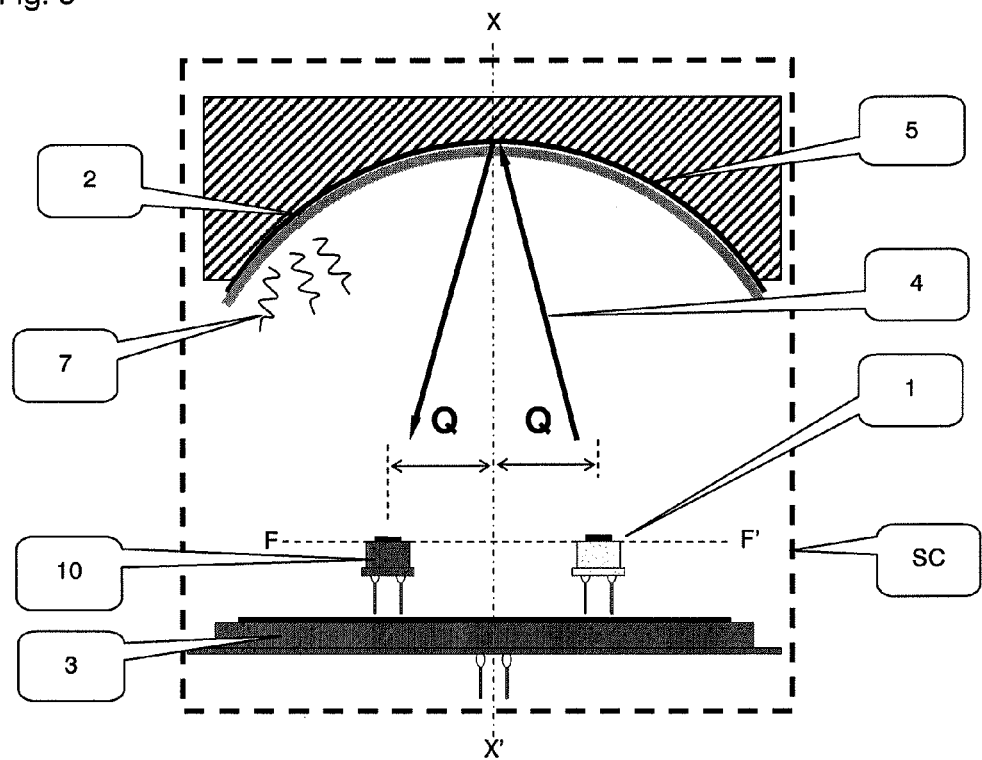
FIG. 8 illustrates a fifth embodiment of a gas sensor.

The same principles are applied in a fifth embodiment, depicted in FIG. 8. Here, the optical geometry is identical to that of the second embodiment and thus will not be described again. However, here the radiation mask positioned to receive the focussed source radiation 4 from LED 1 takes the form of a source radiation detector 10. Thus the detector 10 both shields the underlying luminescence detector assembly from the source radiation 4 and generates a reference signal $S_R$. This configuration is particularly advantageous since all of the electrical components are provided on one side of the sensor and thus can be placed on a single PCB or otherwise formed as a unitary component. This enables the sensor to be made on a standard production line, and makes the design particularly well suited for production in large volumes. Again, the luminescence detector assembly 3 need not lie in a second plane but could be laterally offset in the same plane as the source radiation detector 10 and LED 1, e.g. formed as a component array in the manner of that shown in FIG. 5.

In both of the fourth and fifth embodiments, it is preferred that the reference signal generated by the source radiation detector is not influenced by the luminescence emitted by the gas-sensitive material. However, this is not essential since the source radiation will typically have a magnitude several times that of the luminescence and so will dominate the generated signal. Nonetheless, it may be advantageous to position the detector 10 at a location in which little or no luminescence will be incident thereon (e.g. behind the mirror 5, as in FIG. 7). Alternatively, an optical filter 10a may be provided to block the luminescent wavelength $\lambda_2$ from reaching the detector 10. Since the influence of the luminescence is small, however, a high quality filter is not required.

Figure 10:
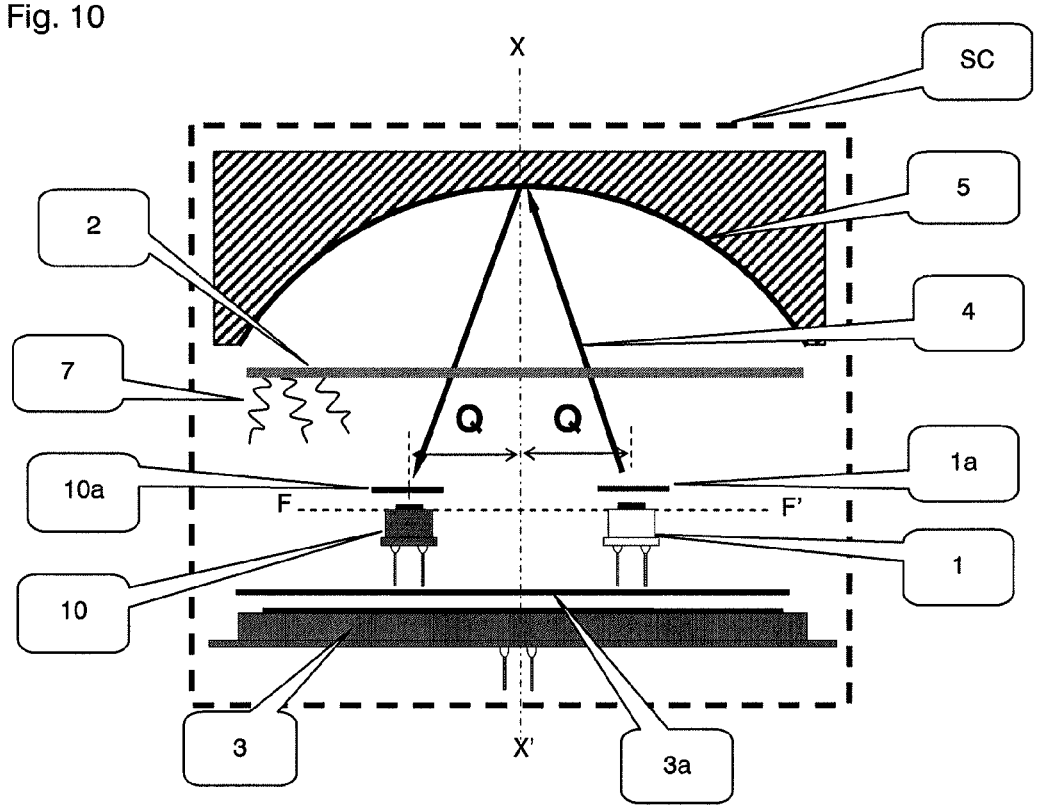
FIG. 10 illustrates a sixth embodiment of a gas sensor.

FIG. 10 depicts a sixth embodiment of a gas sensor which is a variant of that shown in FIG. 8. The optical geometry is identical and will not be described again. The sensor operates on the same principles already discussed with reference to FIG. 8, despite a number of modifications which could be applied to any of the embodiments above. Firstly, the photoluminescent material 2 is not disposed on the surface of mirror 5 but rather is carried on a transparent support film (not shown). The material 2 could be positioned at any location within the gas sample chamber SC at which it will receive source radiation 4 (either directly from the source 1, or redirected by optics assembly 5), but preferably is disposed between the source 1 and the optics assembly such that source radiation will pass through the material at least twice, leading to improvements in the sensor efficiency as discussed above. The sixth embodiment also provides the advantage that both sides of the luminescent layer 2 can be exposed to the target gas, so the surface area of the sensitive material and, accordingly, the intensity of emitted luminescence is increased: for instance, an emitted intensity around two times larger than in the previous embodiments may be expected.

Whilst the photoluminescent material 2 must be located in the sample chamber SC in order to respond to changes in the target gas concentration, it should be noted that the other components could be provided externally to the chamber, provided the walls of the chamber are transparent to the relevant wavelengths or include appropriate transparent windows.

The FIG. 10 embodiment also includes a number of additional optical filters 1a, 3a and 10a. As explained above, if the optics assembly is configured to converge source radiation to a suitably high degree (e.g. a focussed image of the source 1 is produced at a location which does not overlap the luminescence detector assembly 3 to any extent), it may be possible to omit the filters entirely. However, usually the focusing/converging will not be absolute and thus a small amount of source radiation may be incident on the detector assembly 3. It may therefore be advantageous to provide the sensor with one or more of the optical filters shown in FIG. 10. Filter 1a is provided to filter the radiation emitted by source 1. This may be appropriate where the source has a relatively wide emission spectrum which could include the luminescence wavelength $\lambda_2$. Any filtering of this wavelength must be carried out at the source 1 rather than at the detector assembly 3 since the detector assembly 3 must remain responsive to radiation of the same wavelength emitted by the gas-sensitive material 2. A second filter 3a may be provided to filter radiation arriving at the detector assembly 3 to remove other source wavelengths. Since the amount of source radiation incident on the luminescence detector assembly 3 is greatly reduced by way of the converging optics assembly, however, the filters 1a and 3a need not be highly absorbent of the relevant wavelengths: for instance, inexpensive semi-transparent polymer films of the appropriate colours may suffice. Where the components are mounted into a casing to form an array as mentioned above, the casing may be formed of appropriately coloured plastics materials in order to perform the desired filtering functions.

The invention claimed is:

1. A gas sensor comprising:
a chamber for containing a gas sample in use; a radiation source adapted to emit radiation within a first waveband; within the chamber and positioned to receive radiation from the radiation source, a photoluminescent material which, upon absorption of radiation of a first wavelength within the first waveband, emits radiation of a second wavelength, the photoluminescent material being responsive to the presence of a target gas species in the gas sample such that the intensity of the emitted radiation varies according to the concentration of the target gas species in the gas sample;
a luminescence detector assembly positioned at a first location at which radiation emitted by the photoluminescent material can be received, the luminescence detector assembly being adapted to detect radiation of the second wavelength and output a corresponding measurement signal related to the concentration of the target gas species in the gas sample; and an optics assembly adapted to receive radiation emitted by the radiation source and to converge the radiation away from the first location and towards a second, different, location at which the luminescence detector assembly cannot receive radiation.

2. A gas sensor according to claim 1, wherein the photoluminescent material, the optics assembly and the luminescence detector assembly are positioned relative to one another such that the luminescence detector assembly receives radiation emitted by the photoluminescent material which has not undergone convergence by the optics assembly.

3. A gas sensor according to claim 1, wherein the photoluminescent material, the optics assembly and the luminescence detector assembly are positioned relative to one another such that the luminescence detector assembly receives radiation directly from the photoluminescent material which has not been passed via the optics assembly.

4. A gas sensor according to claim 1, wherein the optics assembly is a focussing optics assembly adapted to focus radiation received from the radiation source on to the second location.

5. A gas sensor according to claim 1, wherein the luminescence detector assembly is absent at the second location.

6. A gas sensor according to claim 1, wherein the optics assembly is a reflective optics assembly adapted to reflect radiation received from the radiation source such that the second location towards which the radiation is converged is on the same side of the optics assembly as the radiation source.

7. A gas sensor according to claim 6, wherein the luminescence detector assembly is positioned on the same side of the optics assembly as the radiation source and the second location, the first location at which radiation emitted by the photoluminescent material can be received by the luminescence detector assembly being laterally offset from the second location in a direction perpendicular to the optic axis of the optics assembly.

8. A gas sensor according to claim 7, wherein in a lateral plane perpendicular to the optic axis of the optics assembly, the first location at which luminescence can be received by the luminescence detector assembly substantially surrounds the second location.

9. A gas sensor according to claim 6, wherein the photoluminescent material is disposed between the radiation source and the reflective optics assembly such that radiation passes through the material at least twice from the radiation source to the second location.

10. A gas sensor according to claim 6, wherein the second location is coincident with the radiation source, such that the optics assembly converges the reflected radiation towards the radiation source.

11. A gas sensor according to claim 10, wherein the radiation source is positioned between the luminescence detector assembly and the optics assembly, the radiation source obstructing the converged radiation from reaching the luminescence detector assembly.

12. A gas sensor according to claim 10, wherein the radiation source and luminescence detector assembly are located in substantially the same lateral plane perpendicular to the optic axis of the optics assembly.

13. A gas sensor according to claim 6, wherein the optics assembly comprises a concave mirror or a converging lens system and mirror in combination.

14. A gas sensor according to claim 13, wherein the concave mirror comprises a dome-shaped mirror, at least a section of a spherical mirror, a hemispherical mirror, an elliptical mirror or a parabolic mirror.

15. A gas sensor according to claim 13, wherein the optics assembly comprises a concave mirror which subtends a solid angle at the radiation source greater than or equal to the angular spread of the radiation emitted from the source.

16. A gas sensor according to claim 1, wherein a radiation mask is positioned at the second location, such that the optics assembly converges the radiation towards the radiation mask.

17. A gas sensor according to claim 16, wherein the radiation mask is adapted to absorb radiation of at least the first wavelength, preferably radiation across the waveband emitted by the radiation source.

18. A gas sensor according to claim 16, wherein the radiation mask is positioned between the luminescence detector assembly and the optics assembly, the radiation mask obstructing the converged radiation from reaching the luminescence detector assembly.

19. A gas sensor according to claim 16, wherein the optics assembly is a reflective optics assembly adapted to reflect radiation received from the radiation source such that the second location towards at which the radiation mask is positioned is on the same side of the optics assembly as the radiation source.

20. A gas sensor according to claim 19, wherein the radiation source and radiation mask are located in substantially the same lateral plane perpendicular to the optics assembly.

21. A gas sensor according to claim 20, wherein the lateral plane in which the radiation source and radiation mask are positioned is a focal plane of the optics assembly.

22. A gas sensor according to claim 16, wherein the radiation mask comprises a source radiation detector adapted to detect radiation within the first waveband and to output a corresponding signal representing a reference signal.

23. A gas sensor according to claim 1 further comprising a source radiation detector positioned at a third location at which radiation emitted by the radiation source can be received, the source radiation detector being adapted to detect radiation within the first waveband and to output a corresponding signal representing a reference signal.

24. A gas sensor according to claim 23, wherein the optics assembly is a reflective optics assembly adapted to reflect radiation received from the radiation source such that the second location towards at which the radiation mask is positioned is on the same side of the optics assembly as the radiation source, the reflective optics assembly having a non-reflective window through which a portion of the radiation emitted from the radiation source may be transmitted to the third location.

25. A gas sensor according to claim 1, wherein the photoluminescent material is disposed on a surface of the optics assembly.

26. A gas sensor according to claim 1, wherein the optics assembly is a reflective optics assembly having an axis of rotational symmetry, the radiation source and second location being disposed on the axis of rotational symmetry.

27. A gas sensor according to claim 1, wherein the optics assembly is a reflective optics assembly having an axis of rotational symmetry, the radiation source and second location being laterally offset from the axis of rotational symmetry by equal and opposite amounts.

28. A gas sensor according to claim 1, wherein the luminescence detector assembly comprises a plurality of detectors.

29. A gas sensor according to claim 1, wherein the luminescence detector assembly, radiation source and radiation mask if provided form an array in substantially the same plane.

30. A gas sensor according to claim 1, wherein the optics assembly converges radiation towards multiple discrete second locations at which radiation cannot be detected by the luminescence detector assembly.

31. A gas sensor according to claim 1, further comprising a filter positioned to filter radiation arriving at the luminescence detector assembly and adapted to obstruct the passage of radiation in the first waveband.

32. A gas sensor according to claim 1, further comprising a filter positioned to filter radiation emitted by the radiation source to obstruct the passage of radiation of the second wavelength.

33. A gas sensor according to claim 1, wherein the radiation source comprises a LED, laser diode, defocused laser diode or incandescent bulb.

34. A gas sensor according to claim 1, further comprising a source radiation detector positioned at the second location or a third location at which radiation emitted by the radiation source can be received, the source radiation detector being adapted to detect radiation within the first waveband and to output a corresponding signal representing a reference signal, and a processor adapted to compute the ratio between the measurement signal and the reference signal and to output a normalised measurement signal based on the ratio.

35. A gas sensor comprising:
a chamber for containing a gas sample in use;
a radiation source adapted to emit radiation within a first waveband, the radiation being emitted across a first solid angle;
within the chamber and positioned to receive radiation from the radiation source, a photoluminescent material which, upon absorption of radiation of a first wavelength within the first waveband, emits radiation of a second wavelength, the photoluminescent material being responsive to the presence of a target gas species in the gas sample such that the intensity of the emitted radiation varies according to the concentration of the target gas species in the gas sample;
a luminescence detector assembly positioned at a first location at which radiation emitted by the photoluminescent material can be received, the luminescence detector assembly being adapted to detect radiation of the second wavelength and output a corresponding measurement signal related to the concentration of the target gas species in the gas sample; and
a concave mirror assembly adapted to direct radiation from the radiation source towards the photoluminescent material, wherein the concave mirror assembly subtends a solid angle at the radiation source substantially equal to or greater than the first solid angle such that substantially all of the radiation emitted by the source is directed towards the photoluminescent material.

36. A gas sensor according to claim 35, wherein the photoluminescent material is disposed between the radiation source and the reflective optics assembly such that radiation from the source passes through the material at least twice.

37. A gas sensor according to claim 35, wherein the concave mirror assembly subtends a solid angle at the radiation source of at least $\pi/2$, preferably at least $\pi$, still preferably at least $2\pi$.

38. A gas sensor according to claim 35, wherein the concave mirror assembly comprises a dome-shaped mirror, at least a section of a spherical mirror, a hemispherical mirror, an elliptical mirror, a parabolic mirror, or a prismatic mirror.

39. A gas sensor according to claim 35, further comprising a filter positioned to filter radiation arriving at the luminescence detector assembly and adapted to obstruct the passage of radiation in the first waveband.

40. A gas sensor according to claim 35, further comprising a filter positioned to filter radiation emitted by the radiation source to obstruct the passage of radiation of the second wavelength.

41. A gas sensor comprising:
a chamber for containing a gas sample in use;
a radiation source adapted to emit radiation within a first waveband;
within the chamber and positioned to receive radiation from the radiation source, a photoluminescent material which, upon absorption of radiation of a first wavelength within the first waveband, emits radiation of a second wavelength, the photoluminescent material being responsive to the presence of a target gas species in the gas sample such that the intensity of the emitted radiation varies according to the concentration of the target gas species in the gas sample;
a luminescence detector assembly positioned to receive radiation emitted by the photoluminescent material, the luminescence detector assembly being adapted to detect radiation of the second wavelength and output a corresponding measurement signal related to the concentration of the target gas species in the gas sample;
a source radiation detector assembly positioned to receive radiation emitted by the radiation source and adapted to detect radiation of the first waveband and output a corresponding reference signal; and
a processor adapted to compute the ratio between the measurement signal and the reference signal and to output a normalised measurement signal based on the ratio.

42. A gas sensor according to claim 41, further comprising a filter positioned to filter radiation arriving at the luminescence detector assembly and adapted to obstruct the passage of radiation in the first waveband.

43. A gas sensor according to claim 41, further comprising a filter positioned to filter radiation emitted by the radiation source to obstruct the passage of radiation of the second wavelength.

44. A gas sensor according to claim 41, further comprising a filter positioned to filter radiation arriving at the source radiation detector assembly to obstruct the passage of radiation of the second wavelength.

* * * * *